US00PP24303P2

(12) United States Plant Patent
Mak

(10) Patent No.: US PP24,303 P2
(45) Date of Patent: Mar. 11, 2014

(54) LILY PLANT NAMED 'SUNNY GRENADA'

(50) Latin Name: *Lilium hybrida*
Varietal Denomination: Sunny Grenada

(75) Inventor: Niels Johannes Cornelis Mak, Wieringerwerf (NL)

(73) Assignee: Mak Breeding Rights B.V., Wieringerwerf (NL)

( * ) Notice: Subject to any disclaimer, the term of this patent is extended or adjusted under 35 U.S.C. 154(b) by 8 days.

(21) Appl. No.: 13/507,523

(22) Filed: Jul. 5, 2012

(51) Int. Cl.
*A01H 5/00* (2006.01)

(52) U.S. Cl.
USPC ..... Plt./315

(58) Field of Classification Search
USPC ..... Plt./315
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of Lily plant named 'Sunny Grenada', characterized by its upright and compact plant habit; vigorous growth habit; densely-foliated habit; freely flowering habit; upright flower buds; red purple-colored flowers with white-colored margins; and good postproduction longevity.

1 Drawing Sheet

Botanical designation: *Lilium hybrida.*
Cultivar denomination: 'SUNNY GRENADA'.

BACKGROUND OF THE INVENTION

The present Invention relates to a new and distinct cultivar of Lily plant, commercially known as Oriental Hybrid Lily, botanically known as *Lilium hybrida* and hereinafter referred to by the name 'Sunny Grenada'.

The new Oriental Hybrid Lily plant is a product of a planned breeding program conducted by the Inventor in Wieringerwerf, The Netherlands. The objective of the breeding program is to develop new compact and dense potted Oriental Hybrid Lily plants with large flowers, attractive flower coloration and good postproduction longevity.

The new Oriental Hybrid Lily plant originated from a cross-pollination in 2000 of two different unnamed proprietary seedling selections of *Lilium hybrida*, not patented. The new Oriental Hybrid Lily plant was discovered and selected by the Inventor as a single flowering plant from within the resultant progeny of the cross-pollination in a controlled greenhouse environment in Wieringerwerf, The Netherlands in June, 2004.

Asexual reproduction of the new Oriental Hybrid Lily plant by bulb scales in a controlled greenhouse environment in Wieringerwerf, The Netherlands since December, 2007 has shown that the unique features of this new Oriental Hybrid Lily plant are stable and reproduced true to type in successive generations.

SUMMARY OF THE INVENTION

Plants of the new Oriental Hybrid Lily have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunny Grenada'. These characteristics in combination distinguish 'Sunny Grenada' as a new and distinct Oriental Hybrid Lily plant:

1. Upright and compact plant habit.
2. Vigorous growth habit.
3. Densely-foliated habit.
4. Freely flowering habit.
5. Upright flower buds.
6. Red purple-colored flowers with white-colored margins.
7. Good postproduction longevity.

Plants of the new Oriental Hybrid Lily differ primarily from plants of the female parent seedling selection in the following characteristics:

1. Plants of the new Oriental Hybrid Lily have larger leaves than plants of the female parent seedling selection.
2. Flowers of plants of the new Oriental Hybrid Lily are not as upright facing as flowers of plants of the female parent seedling selection.

Plants of the new Oriental Hybrid Lily differ primarily from plants of the male parent seedling selection in the following characteristics:

1. Plants of the new Oriental Hybrid Lily have smaller flowers than plants of the male parent seedling selection.
2. Plants of the new Oriental Hybrid Lily and the male parent seedling selection differ in flower color as plants of the male parent seedling selection have reddish pink-colored flowers.

Plants of the new Oriental Hybrid Lily can be compared to plants of Oriental Hybrid Lily 'After Eight', not patented. Plants of the new Oriental Hybrid Lily differ from plants of 'After Eight' in the following characteristics:

1. Plants of the new Oriental Hybrid Lily have smaller leaves than plants of 'After Eight'.
2. Plants of the new Oriental Hybrid Lily have smaller flowers than plants of 'After Eight'.

3. Flowers of plants of the new Oriental Hybrid Lily are darker in color than flowers of plants of 'After Eight'.

DESCRIPTION OF THE PHOTOGRAPH

The accompanying colored photograph illustrates the overall appearance of the new Oriental Hybrid Lily plant showing the colors as true as it is reasonably possible to obtain in colored reproductions of this type. Colors in the photograph may differ slightly from the color values cited in the detailed botanical description which accurately describe the colors of the new Oriental Hybrid Lily plant. The photograph comprises a side perspective view of a typical flowering plant of 'Sunny Grenada'.

DETAILED BOTANICAL DESCRIPTION

The aforementioned photograph and following observations and measurements describe plants that were grown during the spring in ground beds and 15-cm containers in a glass-covered greenhouse in Wieringerwerf, The Netherlands and under cultural conditions typically used in Oriental Hybrid Lily production. During the production of the plants, day temperatures averaged 15° C., night temperatures averaged 18° C. and light levels averaged 6,000 lux. Measurements and numerical values represent averages for typical flowering plants. Plants were 110 days old when the photograph and description were taken. In the following description, color references are made to The Royal Horticultural Society Colour Chart, 2007 Edition, except where general terms of ordinary dictionary significance are used.

Botanical classification: *Lilium hybrida* 'Sunny Grenada'.

Parentage:

*Female, or seed, parent*.—Unnamed proprietary seedling selection of *Lilium hybrida*, not patented.

*Male, or pollen, parent*.—Unnamed proprietary seedling selection of *Lilium hybrida*, not patented.

Plant description:

*Plant form and growth habit*.—Upright flowering plant; single erect flowering stem with a terminal cluster of flowers; compact and dense plant habit; vigorous growth habit.

*Plant height, soil level to top of flowers*.—About 39 cm.

*Plant diameter or spread*.—About 22 cm.

*Plant circumference*.—About 70 cm.

*Bulbs*.—Diameter: About 10 cm to 20 cm. Texture: Smooth. Color: Close to 155D.

*Flowering stems*.—Diameter: About 9 mm. Internode length: About 2.5 cm. Strength: Strong. Texture: Smooth, glabrous. Color: Close to 138B.

*Leaves*.—Arrangement and quantity: Alternate; simple; sessile; about 36 leaves develop per plant. Length, upper leaves: About 15 cm. Width, upper leaves: About 5 cm. Length, lower leaves: About 7.5 cm. Width, lower leaves: About 2.5 cm. Shape: Lanceolate. Apex: Acute. Base: Decurrent. Margin: Entire. Texture, upper and lower surfaces: Glabrous, smooth; leathery. Venation pattern: Parallel. Color: Developing and fully expanded leaves, upper surface: Close to 137B; venation, close to 137B. Developing and fully expanded leaves, lower surface: Close to 139A; venation, close to 139A.

Flower description:

*Flower shape and aspect*.—Flowers umbellate or funnel-shaped; when fully opened, flowers flatten and tepals recurve towards the apex; flower buds face upright and flowers face upright to outwardly.

*Flowering habit*.—Freely flowering habit, large bulbs will produce six to nine flowers per flowering stem.

*Fragrance*.—Slightly fragrant.

*Natural flowering season*.—Plants flower in June and July in The Netherlands; plants can be flowered year-round in the greenhouse and forced to bloom about 100 days after planting bulbs.

*Postproduction longevity*.—Good postproduction longevity, flowers last about 10 to 15 days on the plant; tepals not persistent; gynoecium persistent.

*Flower buds*.—Length: About 10 cm. Diameter: About 3 cm. Circumference: About 10 cm. Shape: Lanceolate. Color: Close to 144C; color becoming closer to 64A with development; sutures, close to 144C and 64A.

*Flower size*.—Diameter: About 18 cm. Length (height): About 5 cm.

*Perianth*.—Quantity and arrangement: Six tepals per flower arranged in two whorls; tepals imbricate. Tepal length, inner tepals: About 12 cm. Tepal width, inner tepals: About 4 cm. Tepal length, outer tepals: About 11.5 cm. Tepal width, outer tepals: About 5.5 cm. Tepal shape: Lanceolate. Tepal apex: Acute. Tepal margin: Entire; slightly undulating. Tepal texture, upper and lower surfaces: Smooth, glabrous. Tepal color: When opening and fully opened, upper surface: Close to 60A; margins, close to 155D; towards the base, close to 144C; spots, close to 187A; color becoming closer to 187C with development. When opening and fully opened, lower surface: Close to 64A.

*Pedicels*.—Angle: About 45° to 70° from vertical. Strength: Strong. Length: About 3 cm. Diameter: About 5 mm. Texture: Smooth, glabrous. Color: Close to 143A.

*Reproductive organs*.—Stamens: Quantity per flower: Six. Filament length: About 7.3 cm. Filament color: Between 155D and 149B. Anther length: About 1.6 cm. Anther color: Close to 187B. Pollen color: Close to 171A. Pistils: Quantity per flower: One. Style length: About 6.5 cm. Style color: Between 144C and 143B. Stigma diameter: About 7 mm. Stigma shape: Lobed. Stigma color: Close to 83C.

*Fruits*.—Length: About 2.2 cm. Diameter: About 5 mm. Color: Close to 144D.

*Seeds*.—No viable seeds have been observed on plants of the new Oriental Hybrid Lily plant.

Disease & pest resistance: Resistance to pathogens and pests common to Oriental Hybrid Lilies has not been observed on plants of the new Oriental Hybrid Lily.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Sunny Grenada' as illustrated and described.

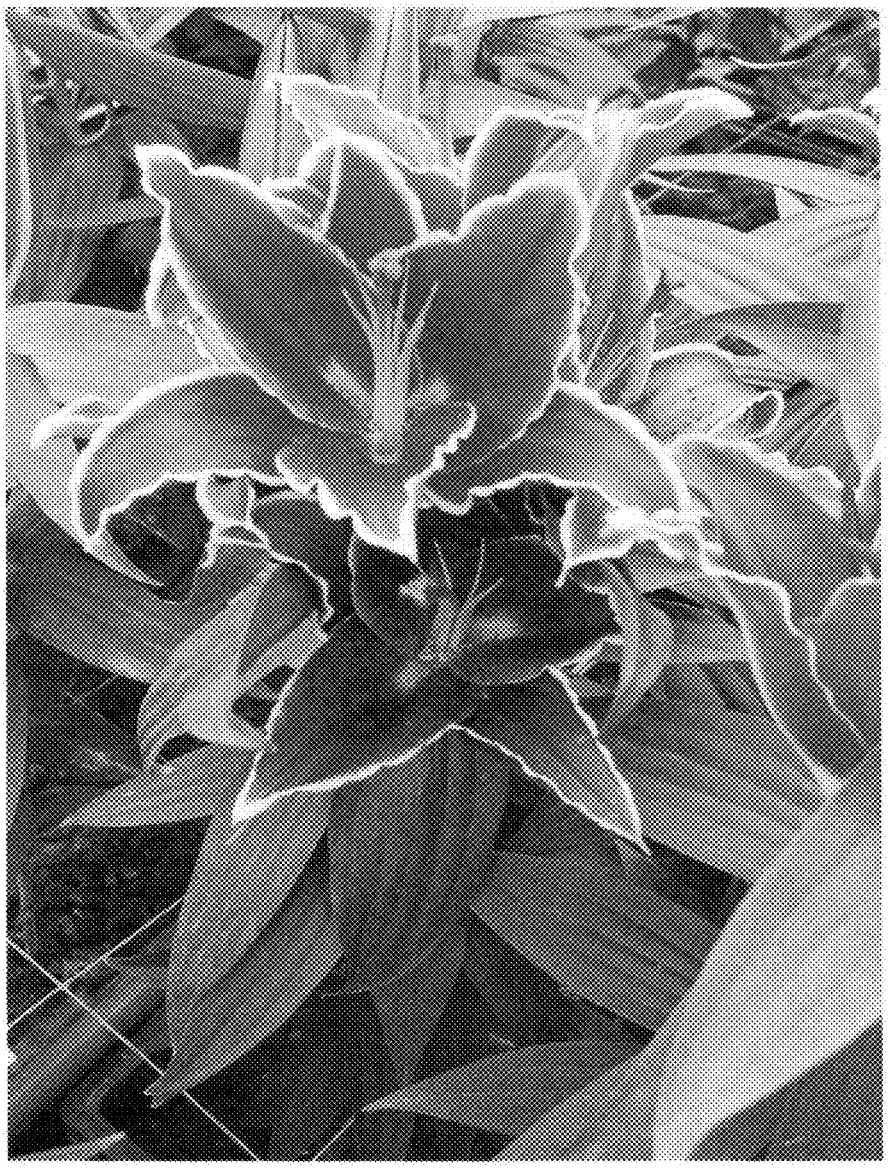

* * * * *